(12) United States Patent
Schulte et al.

(10) Patent No.: US 9,249,404 B2
(45) Date of Patent: Feb. 2, 2016

(54) COAGULATION FACTOR X POLYPEPTIDES WITH MODIFIED ACTIVATION PROPERTIES

(75) Inventors: Stefan Schulte, Marburg (DE); Hans-Peter Hauser, Marburg (DE); Uwe Kalina, Marburg (DE); Thomas Weimer, Gladenbach (DE)

(73) Assignee: CSL Behring GmbH, Marburg (DE)

( * ) Notice: Subject to any disclaimer, the term of this patent is extended or adjusted under 35 U.S.C. 154(b) by 1547 days.

(21) Appl. No.: 11/921,399

(22) PCT Filed: May 30, 2006

(86) PCT No.: PCT/EP2006/005131
§ 371 (c)(1),
(2), (4) Date: Jan. 24, 2008

(87) PCT Pub. No.: WO2006/128668
PCT Pub. Date: Dec. 7, 2006

(65) Prior Publication Data
US 2009/0053185 A1 Feb. 26, 2009

Related U.S. Application Data

(60) Provisional application No. 60/688,704, filed on Jun. 9, 2005.

(30) Foreign Application Priority Data

Jun. 1, 2005 (EP) ..................... 05011773

(51) Int. Cl.
*C12N 9/64* (2006.01)
*C12N 15/57* (2006.01)
*A61K 38/48* (2006.01)

(52) U.S. Cl.
CPC ....... *C12N 9/6432* (2013.01); *C12Y 304/21006* (2013.01)

(58) Field of Classification Search
None
See application file for complete search history.

(56) References Cited

U.S. PATENT DOCUMENTS

| | | | |
|---|---|---|---|
| 4,501,731 A | 2/1985 | Tishkoff et al. | |
| 4,784,950 A | 11/1988 | Hagen et al. | |
| 6,562,598 B1 | 5/2003 | Himmelspach et al. | |
| 6,573,071 B1 | 6/2003 | Himmelspach et al. | |
| 7,329,724 B2 | 2/2008 | Araki et al. | |

FOREIGN PATENT DOCUMENTS

| | | |
|---|---|---|
| FR | 2 841 904 A1 | 1/2004 |
| WO | WO 98/38317 | 9/1998 |
| WO | WO 98/38318 | 9/1998 |
| WO | WO 98/39456 A1 | 9/1998 |
| WO | WO 01/10896 A2 | 2/2001 |
| WO | WO 03/006054 | 1/2003 |
| WO | WO 03/035861 | 5/2003 |
| WO | WO 2004/005347 | 1/2004 |
| WO | WO 2006/128668 | 12/2006 |

OTHER PUBLICATIONS

Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Torchilin et al, Peptide and protein drug delivery to and into tumors: challenges and solutions, DDT, 2003, vol. 8(6), pp. 259-266.*
Wang, Wei, Instability, stabilization and formulation of liquid protein pharmaceuticals, Int. J. Pharm, 1999, vol. 185, pp. 129-188.*
Camire et al. (2000) "Enhanced y-Carboxylation of Recombinant Factor X Using a Chimeric Construct Containing the Prothrombin Propeptide ," *Biochemistry* 39:14332-14329.
Erhardtsen (2002) "To General Haemostasis—the Evidence-Based Route," *Pathophysiol. Haemost Thromb* 32:47-52.
Himmelspach et al. (2002) "A Fully Recombinant Partial Prothrombin Complex Effectively Bypasses fVIII In Vitro and In Vivo," *Thromb. Haemost*. 88:1003-1011.
Leytus et al. (1984) "Characterization of a cDNA coding for human factor X," *Proc. Natl. Acad. Sci. USA* 81:3699-3702.
Ni et al. (1992) "Normalization of the Haemostatic Plugs of Dogs with Haemophilia A (Factor VII Deficiency) Following the Infusion of a Combination of Factor Xa and Phosphatidylcholine/Phosphatidylserine Vesicles," *Thromb. Haemost*. 67:264-271.
O'Reilly et al. (1999) "Antiangiogenic Activity of the Cleaved Conformation of the Serpin Antithrombin," *Science* 285:1926-1928.
Rudolph et al. (1997) "Expression, Purification, and Characterization of Recombinant Human Factor X," *Prot. Express and Puri*. 10:373-378.
Rudolph et al. (2002) "The Role of the Factor X Activation Peptide: A Deletion Mutagenesis Approach," *Thromb. Haemost*. 88:756-62.
Thiec et al. (2003) "Role of the Gla and First Epidermal Growth Factor-like Domains of Factor X in the Prothrombinase and Tissue Factor-Factor VIIa Complexes," *J. Biol. Chem*. 278(12):10393-10399.

(Continued)

*Primary Examiner* — Maria Marvich
(74) *Attorney, Agent, or Firm* — Finnegan, Henderson, Farabow, Garrett & Dunner, LLP

(57) ABSTRACT

The present invention relates to modified cDNA sequences coding for human Factor X and their derivatives with improved stability and modified activation sequences, recombinant expression vectors containing such cDNA sequences, and host cells transformed with such recombinant expression vectors. The invention also relates to recombinant factor X polypeptides and derivatives which have biological activities of the unmodified wild type protein but with improved stability and processes for the manufacture of such recombinant proteins and their derivatives. The invention also covers a transfer vector for use in human gene therapy, which comprises such modified DNA.

9 Claims, 5 Drawing Sheets

(56) References Cited

OTHER PUBLICATIONS

Völkel et al. (2005) "Engineering of Human Coagulation Factor X Variants Activated by Prostate-Specific Antigen," *Mol. Biotechnol.* 29:19-30.

Wolf et al. (1991) "Design of Constructs for the Expression of Biologically Active Recombinant Human Factors X and Xa," *J. Biol. Chem.* 266(21), pp. 13726-13730.

Wolf et al. (1995) "Procoagulant Activity of Reversibly Acylated Human Factor Xa," *Blood* 86:4153-4157.

Völkel et al.; "Engineering of Factor X Variants Activated by Prostate-Specific Antigen", Journal of Cancer Research and Clinical Oncology, XP009054576, ISSN: 0171-5216, Abstract, vol. 127, No. Suppl 1, p. S69, (2001).

"Hemostasis and Thrombosis, Basic Principles and Clinical Practice", Fourth Edition, Colman et al., 2001, factor IIa: p. 34-35, p. 176, factor IXa: p. 40-41, factor Xa: p. 34-35, factor XIa: p. 128-129, factor XIIa: p. 194, aPC: p. 34-35, p. 159, kallikrein: p. 103-104.

Bettini et al., Book review of "Handbook of Pharmaceutical Excipients, Third Edition, Arthur H. Kibbe (ed.), Pharmaceutical Press, London, 2000, 665 pp.," Book reviews / Journal of Controlled Release 71, pp. 352-353 (2001).

Lee, G., Book review of "Pharmaceutical Formulation Development of Peptides and Proteins, Sven Frokjaer, Lars Hovgaard, Taylor & Francis, Andover, UK, 2000, 238 pp.," Book reviews / European Journal of Pharmaceutics and Biopharmaceutics 50, p. 329 (2000).

Chang, Y.J., et al., "Indentification of functionally important residues of the epidermal growth factor-2 domain of factor IX by alanine-scanning mutagenesis. Residues Asn(89)-Gly(93) are critical for binding factor VIIIa," *J. Biol. Chem.* 277(28): 25393-9 (2002). (abstract only).

Hertzberg, M., "Biochemistry of Factor X," *Blood Review* 8: 56-62 (1994).

Peyvandi, F., et al., "Gene mutations and three-dimensional structural analysis in 13 families with severe factor X deficiency," *Br. J. Haematol.* 117(3): 685-92 (2002). (abstract only).

Venkateswarlu, D., et al., "Structure and Dynamics of Zymogen Human Blood Coagulation Factor X," *Biophysical Journal* 82: 1190-1206 (2002).

Richard, F.M., "Protein stability: still an unsolved problem," *Cell Mol. Life Sci.* 53:790-80 (1997).

Bianchini et al., "Mapping of the Catalytic Groove Preferences of Factor Xa Reveals an Inadequate Selectivity for Its Macromolecule Substrates," *The Journal of Biological Chemistry*, 277(23):20527-20534 (2002).

Courter et al., "Clinical Evaluation of B-Domain Deleted Recombinant Factor VIII in Previously Untreated Patients," *Seminars in Hematology*, 38(2)Suppl 4:52-59 (2001).

Dingli et al., "Continuous factor VIII infusion therapy in patients with haemophilia A undergoing surgical procedures with plasma-derived or recombinant factor VIII concentrates," *Haemophilia*, 8:629-634 (2002).

Hertzberg, Mark, "Biochemistry of Factor X," *Blood Reviews*, 8:56-62 (1994).

Himmelspach et al., "Recombinant Human Factor X: High Yield Expression and the Role of Furin in Proteolytic Maturation in Vivo and in Vitro," *Thrombosis Research*, 97:51-67 (2000).

Hoots et al., "Continuous intravenous infusion of a plasma-derived factor IX concentrate (Mononine®) in haemophilia B," *Haemophilia*, 9:164-172 (2003).

Midathada et al., "Recombinant Factor VIIa in the Treatment of Bleeding," *Am. J. Clin. Pathol.*, 121:124-137 (2004).

Ragni et al., "Use of recombinant factor IX in subjects with haemophilia B undergoing surgery," *Haemophilia*, 8: 91-97 (2002).

Rothschild et al., "European data of a clinical trial with a sucrose formulated recombinant factor VIII in previously treated haemophilia A patients," *Haemophilia*, 8(Suppl. 2):10-14 (2002).

Thiec et al., "Role of the Gla and First Epidermal Growth Factor-like Domains of Factor X in the Prothrombinase and Tissue Factor-Factor VIIa Complexes," *The Journal of Biological Chemistry*, 278(12):10393-10399 (2003).

Uprichard et al., "Factor X deficiency," *Blood Reviews*, 16:97-110 (2002).

Mizuno et al, "Crystal Structure of an anticoagulant protein in complex with the Gla domain of factor X," *PNAS*, 98(13): 7230-7234 (2001).

Rezaie, Alireza R., "Identification of Basic Residues in the Heparin-binding Exosite of Factor Xa Critical for Heparin and Factor Va Binding," *The Journal of Biological Chemistry*, 275(5): 3320-3327 (2000).

* cited by examiner

Figure 1:

Activation Peptide pFX-532  ...TTCAACCAGACGCAGCCTGAGAGGGGCGACAACAACCTCACCAGG
         ...F  N  Q  T  Q  P  E  R  G  D  N  N  L  T  R$_{234}$ pFX-619  ...TTCAACCAGACGCAGCCTGAGAGGGGCGACAACAACCTCACCAGG
         ...F  N  Q  T  Q  P  E  R  G  D  N  N  L  T  R Heavy Chain ATC                                                      GTGGGAGGC...
I$_{235}$                                                 V  G  G...

ATCACCCAGAGCTTCAACGACTTCACCCGCATTGTGGGAGGC...
I  T  Q  S  F  N  D  F  T  R  I  V  G  G...

Figure 2:

| Light Chain | Activation Peptide | Heavy Chain |
|---|---|---|
| rFX-532..R | SVA...FNQTQPERGDNNLTR$_{234}$ I$_{235}$ | VGG... |
| rFX-535..R | SVA...FNQTQPTQSFNDFTR    I | VGG... |
| rFX-641..R | SVA...FNQTQPERGDNN<u>D</u>DR    I | VGG... |
| rFX-619..R | SVA...FNQTQPERGDNNLTR | ITQSFNDFTRIVGG... |
| rFX-635..R | SVA...FNQTQPERGDNN<u>D</u>DR | ITQSFNDFTRIVGG... |

Figure 3: Wild type Factor X cDNA and amino acid sequence

| | | | | | | | | | | | | | | | | |
|---|---|---|---|---|---|---|---|---|---|---|---|---|---|---|---|---|
| atg | ggg | cgc | cca | ctg | cac | ctc | gtc | ctg | ctc | agt | gcc | tcc | ctg | gct | ggc | 48 |
| Met | Gly | Arg | Pro | Leu | His | Leu | Val | Leu | Leu | Ser | Ala | Ser | Leu | Ala | Gly | |
| 1 | | | | 5 | | | | | 10 | | | | | 15 | | |

| ctc | ctg | ctg | ctc | ggg | gaa | agt | ctg | ttc | atc | cgc | agg | gag | cag | gcc | aac | 96 |
|---|---|---|---|---|---|---|---|---|---|---|---|---|---|---|---|---|
| Leu | Leu | Leu | Leu | Gly | Glu | Ser | Leu | Phe | Ile | Arg | Arg | Glu | Gln | Ala | Asn | |
| | | | 20 | | | | | 25 | | | | | 30 | | | |

| aac | atc | ctg | gcg | agg | gtc | acg | agg | gcc | aat | tcc | ttt | ctt | gaa | gag | atg | 144 |
|---|---|---|---|---|---|---|---|---|---|---|---|---|---|---|---|---|
| Asn | Ile | Leu | Ala | Arg | Val | Thr | Arg | Ala | Asn | Ser | Phe | Leu | Glu | Glu | Met | |
| | | 35 | | | | | 40 | | | | | 45 | | | | |

| aag | aaa | gga | cac | ctc | gaa | aga | gag | tgc | atg | gaa | gag | acc | tgc | tca | tac | 192 |
|---|---|---|---|---|---|---|---|---|---|---|---|---|---|---|---|---|
| Lys | Lys | Gly | His | Leu | Glu | Arg | Glu | Cys | Met | Glu | Glu | Thr | Cys | Ser | Tyr | |
| | 50 | | | | | 55 | | | | | 60 | | | | | |

| gaa | gag | gcc | cgc | gag | gtc | ttt | gag | gac | agc | gac | aag | acg | aat | gaa | ttc | 240 |
|---|---|---|---|---|---|---|---|---|---|---|---|---|---|---|---|---|
| Glu | Glu | Ala | Arg | Glu | Val | Phe | Glu | Asp | Ser | Asp | Lys | Thr | Asn | Glu | Phe | |
| 65 | | | | | 70 | | | | | 75 | | | | | 80 | |

| tgg | aat | aaa | tac | aaa | gat | ggc | gac | cag | tgt | gag | acc | agt | cct | tgc | cag | 288 |
|---|---|---|---|---|---|---|---|---|---|---|---|---|---|---|---|---|
| Trp | Asn | Lys | Tyr | Lys | Asp | Gly | Asp | Gln | Cys | Glu | Thr | Ser | Pro | Cys | Gln | |
| | | | | 85 | | | | | 90 | | | | | 95 | | |

| aac | cag | ggc | aaa | tgt | aaa | gac | ggc | ctc | ggg | gaa | tac | acc | tgc | acc | tgt | 336 |
|---|---|---|---|---|---|---|---|---|---|---|---|---|---|---|---|---|
| Asn | Gln | Gly | Lys | Cys | Lys | Asp | Gly | Leu | Gly | Glu | Tyr | Thr | Cys | Thr | Cys | |
| | | | 100 | | | | | 105 | | | | | 110 | | | |

| tta | gaa | gga | ttc | gaa | ggc | aaa | aac | tgt | gaa | tta | ttc | aca | cgg | aag | ctc | 384 |
|---|---|---|---|---|---|---|---|---|---|---|---|---|---|---|---|---|
| Leu | Glu | Gly | Phe | Glu | Gly | Lys | Asn | Cys | Glu | Leu | Phe | Thr | Arg | Lys | Leu | |
| | | | 115 | | | | | 120 | | | | | 125 | | | |

| tgc | agc | ctg | gac | aac | ggg | gac | tgt | gac | cag | ttc | tgc | cac | gag | gaa | cag | 432 |
|---|---|---|---|---|---|---|---|---|---|---|---|---|---|---|---|---|
| Cys | Ser | Leu | Asp | Asn | Gly | Asp | Cys | Asp | Gln | Phe | Cys | His | Glu | Glu | Gln | |
| | 130 | | | | | 135 | | | | | 140 | | | | | |

| aac | tct | gtg | gtg | tgc | tcc | tgc | gcc | cgc | ggg | tac | acc | ctg | gct | gac | aac | 480 |
|---|---|---|---|---|---|---|---|---|---|---|---|---|---|---|---|---|
| Asn | Ser | Val | Val | Cys | Ser | Cys | Ala | Arg | Gly | Tyr | Thr | Leu | Ala | Asp | Asn | |
| 145 | | | | 150 | | | | | 155 | | | | | 160 | | |

| ggc | aag | gcc | tgc | att | ccc | aca | ggg | ccc | tac | ccc | tgt | ggg | aaa | cag | acc | 528 |
|---|---|---|---|---|---|---|---|---|---|---|---|---|---|---|---|---|
| Gly | Lys | Ala | Cys | Ile | Pro | Thr | Gly | Pro | Tyr | Pro | Cys | Gly | Lys | Gln | Thr | |
| | | | | 165 | | | | | 170 | | | | | 175 | | |

| ctg | gaa | cgc | agg | aag | agg | tca | gtg | gcc | cag | gcc | acc | agc | agc | agc | ggg | 576 |
|---|---|---|---|---|---|---|---|---|---|---|---|---|---|---|---|---|
| Leu | Glu | Arg | Arg | Lys | Arg | Ser | Val | Ala | Gln | Ala | Thr | Ser | Ser | Ser | Gly | |
| | | | 180 | | | | | 185 | | | | | 190 | | | |

| gag | gcc | cct | gac | agc | atc | aca | tgg | aag | cca | tat | gat | gca | gcc | gac | ctg | 624 |
|---|---|---|---|---|---|---|---|---|---|---|---|---|---|---|---|---|
| Glu | Ala | Pro | Asp | Ser | Ile | Thr | Trp | Lys | Pro | Tyr | Asp | Ala | Ala | Asp | Leu | |
| | | 195 | | | | | 200 | | | | | 205 | | | | |

| gac | ccc | acc | gag | aac | ccc | ttc | gac | ctg | ctt | gac | ttc | aac | cag | acg | cag | 672 |
|---|---|---|---|---|---|---|---|---|---|---|---|---|---|---|---|---|
| Asp | Pro | Thr | Glu | Asn | Pro | Phe | Asp | Leu | Leu | Asp | Phe | Asn | Gln | Thr | Gln | |
| | 210 | | | | | 215 | | | | | 220 | | | | | |

Figure 3 (continued)

| | |
|---|---|
| cct gag agg ggc gac aac aac ctc acc agg atc gtg gga ggc cag gaa<br>Pro Glu Arg Gly Asp Asn Asn Leu Thr Arg Ile Val Gly Gly Gln Glu<br>225                      230                 235                     240 | 720 |
| tgc aag gac ggg gag tgt ccc tgg cag gcc ctg ctc atc aat gag gaa<br>Cys Lys Asp Gly Glu Cys Pro Trp Gln Ala Leu Leu Ile Asn Glu Glu<br>                 245                     250                     255 | 768 |
| aac gag ggt ttc tgt ggt gga acc att ctg agc gag ttc tac atc cta<br>Asn Glu Gly Phe Cys Gly Gly Thr Ile Leu Ser Glu Phe Tyr Ile Leu<br>                 260                     265                     270 | 816 |
| acg gca gcc cac tgt ctc tac caa gcc aag aga ttc aag gtg agg gta<br>Thr Ala Ala His Cys Leu Tyr Gln Ala Lys Arg Phe Lys Val Arg Val<br>                 275                     280                     285 | 864 |
| ggg gac cgg aac acg gag cag gag gag ggc ggt gag gcg gtg cac gag<br>Gly Asp Arg Asn Thr Glu Gln Glu Glu Gly Gly Glu Ala Val His Glu<br>290                      295                 300 | 912 |
| gtg gag gtg gtc atc aag cac aac cgg ttc aca aag gag acc tat gac<br>Val Glu Val Val Ile Lys His Asn Arg Phe Thr Lys Glu Thr Tyr Asp<br>305                      310                 315                     320 | 960 |
| ttc gac atc gcc gtg ctc cgg ctc aag acc ccc atc acc ttc cgc atg<br>Phe Asp Ile Ala Val Leu Arg Leu Lys Thr Pro Ile Thr Phe Arg Met<br>                 325                     330                     335 | 1008 |
| aac gtg gcg cct gcc tgc ctc ccc gag cgt gac tgg gcc gag tcc acg<br>Asn Val Ala Pro Ala Cys Leu Pro Glu Arg Asp Trp Ala Glu Ser Thr<br>                 340                     345                     350 | 1056 |
| ctg atg acg cag aag acg ggg att gtg agc ggc ttc ggg cgc acc cac<br>Leu Met Thr Gln Lys Thr Gly Ile Val Ser Gly Phe Gly Arg Thr His<br>                 355                     360                     365 | 1104 |
| gag aag ggc cgg cag tcc acc agg ctc aag atg ctg gag gtg ccc tac<br>Glu Lys Gly Arg Gln Ser Thr Arg Leu Lys Met Leu Glu Val Pro Tyr<br>       370                     375                     380 | 1152 |
| gtg gac cgc aac agc tgc aag ctg tcc agc agc ttc atc atc acc cag<br>Val Asp Arg Asn Ser Cys Lys Leu Ser Ser Ser Phe Ile Ile Thr Gln<br>385                      390                 395                     400 | 1200 |
| aac atg ttc tgt gcc ggc tac gac acc aag cag gag gat gcc tgc cag<br>Asn Met Phe Cys Ala Gly Tyr Asp Thr Lys Gln Glu Asp Ala Cys Gln<br>                 405                     410                     415 | 1248 |
| ggg gac agc ggg ggc ccg cac gtc acc cgc ttc aag gac acc tac ttc<br>Gly Asp Ser Gly Gly Pro His Val Thr Arg Phe Lys Asp Thr Tyr Phe<br>                 420                     425                     430 | 1296 |
| gtg aca ggc atc gtc agc tgg gga gag ggc tgt gcc cgt aag ggg aag<br>Val Thr Gly Ile Val Ser Trp Gly Glu Gly Cys Ala Arg Lys Gly Lys<br>                 435                     440                     445 | 1344 |

Figure 3 (continued)

```
tac ggg atc tac acc aag gtc acc gcc ttc ctc aag tgg atc gac agg    1392
Tyr Gly Ile Tyr Thr Lys Val Thr Ala Phe Leu Lys Trp Ile Asp Arg
    450                 455                 460 tcc atg aaa acc agg ggc ttg ccc aag gcc aag agc cat gcc ccg gag    1440
Ser Met Lys Thr Arg Gly Leu Pro Lys Ala Lys Ser His Ala Pro Glu
465                 470                 475                 480 gtc ata acg tcc tct cca tta aag tga                                 1467
Val Ile Thr Ser Ser Pro Leu Lys  *
                485
```

US 9,249,404 B2

COAGULATION FACTOR X POLYPEPTIDES WITH MODIFIED ACTIVATION PROPERTIES

This application is a 35 U.S.C. §371 National Phase Entry application of co-pending International Application PCT/EP2006/005131, filed May 30, 2006, which designated the U.S. and which claims the benefit under 35 U.S.C. §119 of European Application No. 105011773.8, filed Jun. 1, 2005, and claims the benefit of U.S. Application No. 60/688,704, filed Jun. 9, 2005, the entire contents of which are hereby incorporated by reference.

FIELD OF THE INVENTION

The present invention relates to modified cDNA sequences coding for factor X polypeptides, in particular human factor X and its derivatives which can bypass the need for either factor VIIIa/FIXa or factor VIIa/TF for activation. The invention relates further to recombinant expression vectors containing such modified cDNA sequences, host cells transformed with such recombinant expression vectors, recombinant polypeptides and derivatives which do have biological activities of the unmodified wild type protein but having altered activation properties and processes for the manufacture of such recombinant proteins and their derivatives. The invention also covers a transfer vector for use in human gene therapy, which comprises such modified DNA sequences.

BACKGROUND OF THE INVENTION

Vitamin K dependent proteins are used to treat certain types of hemophilia. Classic hemophilia or hemophilia A is an inherited bleeding disorder. It results from a chromosome X-linked deficiency of blood coagulation factor VIII, and affects almost exclusively males with an incidence between one and two individuals per 10,000. The X-chromosome defect is transmitted by female carriers who are not themselves hemophiliacs. The clinical manifestation of hemophilia A is an increased bleeding tendency. Before treatment with factor VIII concentrates was introduced the mean life span for a person with severe hemophilia was less than 20 years. The use of concentrates of factor VIII from plasma and later on that of recombinant forms of factor VIII has considerably improved the situation for the hemophilia patients increasing the mean life span extensively, giving most of them the possibility to live a more or less normal life. Hemophilia B being 5 times less prevalent than hemophilia A is caused by non-functional or missing factor IX and is treated with factor IX concentrates from plasma or a recombinant form of factor IX. In both hemophilia A and in hemophilia B the most serious medical problem in treating the disease is the generation of alloantibodies against the replacement factors. Up to 30% of all hemophilia A patients develop antibodies to factor VIII. Antibodies to FIX occur to a lesser extent but with more severe consequences, as they are less susceptible to immune tolerance induction therapy.

The current model of coagulation states that the physiological trigger of coagulation is the formation of a complex between tissue factor (TF) and factor VIIa (FVIIa) on the surface of TF expressing cells, which are normally located outside the vasculature and only get accessible once an injury occurs. The complex of factor VIIa/TF activates factor IX and factor X ultimately generating some thrombin. In a positive feedback loop thrombin activates factor VIII and factor IX which then also activate factor X, the so-called "intrinsic" arm of the blood coagulation cascade, thus amplifying the generation of factor Xa, which is necessary for the generation of the full thrombin burst to achieve complete hemostasis. It was shown that by administering supraphysiological concentrations of FVIIa hemostasis is achieved bypassing the need for factor VIIIa and factor IXa. The cloning of the cDNA for factor VII (U.S. Pat. No. 4,784,950) made it possible to develop a recombinant replacement of that plasma derived coagulation factor. This factor VIIa was successfully administered for the first time in 1988 to a patient with a high titer of inhibitory antibodies to FVIII. Ever since the number of indications of factor VIIa has grown steadily showing a potential for factor VIIa to become an universal hemostatic agent (Erhardtsen, 2002). Unfortunately factor VIIa has only a plasma half-life of slightly above 2 hours and must thus be readministered frequently making such therapy invasive and very expensive. There is thus an ongoing need for improved coagulation factors, especially such that are haemostatic bypassing agents. Haemostatic bypassing agents are substances, which allow coagulation to occur when administered to patients in whom certain coagulation factors are missing, non-functional or blocked by inhibitory antibodies. The activity of such compounds to bypass blocks in the coagulation cascade (haemostatic bypassing activity) can be measured by coagulation assays known in the art. Essentially haemostatic bypassing agents have the ability to activate substrates of a missing, non-functional or blocked coagulation factor or other substrates in the coagulation cascade "downstream" of the missing, non-functional or blocked coagulation factor in a direct way such that the missing, non-functional or blocked coagulation factor is no longer needed for effective thrombin generation.

Also factor X has been the subject of extensive research.

The cDNA for factor X has been characterized (Leytus et al. 1984, PNAS, 82: 3699-3702). Coagulation factor X is a vitamin-K dependent glycoprotein of a molecular weight of 58.5 kDa, which is secreted from liver cells into the plasma as a zymogen. Initially factor X is produced as a prepropeptide with a signal peptide consisting in total of 488 amino acids. The signal peptide is cleaved off by signal peptidase during export into the endoplasmatic reticulum, the propeptide sequence is cleaved off after gamma carboxylation took place at the first 11 glutamic acid residues at the N-terminus of the mature N-terminal chain. A further processing step occurs by cleavage between Arg182 and Ser183. This processing step also leads concomitantly to the deletion of the tripeptide Arg180-Lys181-Arg182. The resulting secreted factor X zymogen consists of an N-terminal light chain of 139 amino acids ($M_r$ 16,200) and a C-terminal heavy chain of 306 amino acids ($M_r$ 42,000) which are covalently linked via a disulfide bridge between Cys172 and Cys342. Further posttranslational processing steps include the β-hydroxylation of Asp103 as well as N- and O-type glycosylation.

Both factor VIIIa/factor IXa or factor VIIa/TF are under physiological conditions able to activate factor X on activated platelet surfaces by cleaving carboxy-terminal to Arg234, thus liberating the so called activation peptide of 52 amino acids from Ser183 to Arg234.

In an autocatalytic cleavage activated factor X (factor Xa) cleaves off a small fragment at the C-terminal end of its heavy chain carboxy-terminal to Arg464 leading to factor Xaβ. However the physiological relevance of this cleavage is not clear as both forms of factor Xa have comparable catalytic activities.

Several attempts have been made to modify factor X:

Wolf et al. 1991 (JBC. 266, no. 21. pp. 13726-13730) deleted the activation peptide of factor X replacing it with the dipeptide Arg-Lys which leads to the introduction of 2 novel furin cleavage consensus sites within the region of the activation peptide of factor X. Such factor X variants are activated during intracellular processing leading thus to the secretion of activated factor X.

Wolf et al. 1995 (Blood. 86, pp 4153-4157) produced acylated inactive variants of factor Xa, which are slowly deacylated after injection into blood plasma thereby generating activated factor X over time.

Rudolph et al. 1997 (Prot. Express and Puri., 10: 373-378), modified factor X in the region of the propeptide cleavage site and found that replacement of Thr39 by Arg improved the efficacy of propeptide processing in cell culture considerably.

Camire et al. 2000 (Biochemistry. 39 pp. 14322-14329) achieved a higher degree of gamma carboxylation in cell culture by replacing the prepropeptide of factor X by that of thrombin. However though the rate of gamma carboxylation was increased 10-30% of factor X remained uncarboxylated.

Rudolph et al., 2002 (Thromb Haemost., 88:756-62) created factor X variants with deleted activation peptide. It could be seen that such factor X variants were auto-activated in a cofactor independent way and the paper concludes that the primary function of the activation peptide is to prevent spurious activation of FX.

Thiec et al. 2003 (JBC, 12, pp 10393-10399) replaced the Gla domain and the first EGF domain of factor X with the corresponding domain of FIX to investigate the ability of such chimeras to interact productively with the TF/FVIIa complex.

WO 98/38317 (Priority: 27 Feb. 1997) claims factor X analogues with a modification at the site of the natural activation cleavage site between Gly228 and Ile235 such that proteases which do not naturally activate factor X can cleave and activate such factor X analogues.

WO 98/38318 (Priority: 27 Feb. 1997) teaches factor X analogues in which amino acids Arg180 to Arg234 are deleted and amino acids from Gly173 to Arg179 are modified such that proteases, which do not naturally activate FX, can cleave the modified sequence thus activating the factor X analogues described above.

WO 01/10896 (Priority: 10 Aug. 1999) describes factor X analogues, which have substitutions of at least one of the amino acids between Glu226 and Me235. In the example the introduction of a FIX derived activation cleavage site is shown which makes the factor X variant cleavable by FXI.

WO 03/035861 (Priority: 19 Oct. 2001) claims variants of factor X in which the activation peptide has been removed and replaced by the amino acids $P_{10}$ to $P_1$ of fibrinopeptide A creating a chimeric thrombin cleavage site rendering this factor X variant activatable by thrombin.

WO 2004/005347 (Priority: 3 Jul. 2002) teaches variants of factor X which can be activated by thrombin by modifying the residues P3-P2-Pi-Pi'-P2'-P3'which is in wild type factor X Leu-Thr-Arg-Ile-Val-Gly (residues 232-237 of SEQ ID NO: 2) to X-Pro-Arg-Ala-Y-Z.

Volkel et al (2005), Mol. Biotechnol., 29 (1):19-30 teaches the introduction of a novel protease cleavage site in the FX activation peptide such that prostrate specific antigen specifically activates said FX variant.

Though some authors suggested that activated factor X (FXa) might be used as a haemostatic bypassing agent (Ni et al., 1992 (Thromb. Haemost. 67:264-271); Himmelspach et al., 2002 (Thromb. Haemost. 88:1003-1011)) some concerns remain that such pharmaceutical preparations might be thrombogenic and could lead to disseminated intravasal coagulation (DIC).

The therapeutic use of the non-activated zymogen factor X appears to be a much safer approach. U.S. Pat. No. 4,501,731 (priority 27 Jun. 1983) suggests the use of factor X as a haemostatic bypassing agent on its own. In WO 03/006054 (Priority: 10 Jul. 2001) it has been shown in addition that factor X in pharmaceutical compositions is able in combination with FVIIa to enhance the haemostatic efficacy of FVIIa synergistically.

However, as the efficacy of activation of factor X via the intrinsic pathway of coagulation is severely compromised in inhibitor patients whereas the extrinsic pathway of coagulation (due to the restricted availability of tissue factor) seems to be limited to the initiation phase of coagulation it is of advantage to modify factor X in such a way to facilitate its activation in situations in which coagulation is needed and bypassing the need of cofactors of limited availability and/or activity. The variant factor X zymogen must be stable so that it can be produced and administered without activation but that in case coagulatory activity (e.g. thrombin generation) is needed, activation occurs at higher rates without the need of the natural activators of the intrinsic and the extrinsic pathway of coagulation.

It has been described that several authors attempted to generate factor X variants which can be activated by proteases not naturally cleaving and activating FX. These factor X variants either consisted of deletions of the activation peptide and/or the modification of the sequence of the activation peptide preceding the cleavage site at Arg234 optionally also allowing the modification of Ile235. As it has also been shown (Rudolph et al., 2002 (Thromb Haemost., 88:756-62) that a primary effect of the activation peptide of factor X is to prevent autoactivation to FXa, factor X variants with deletions and modifications of the activation peptide are susceptible to premature activation. Pharmaceutical compositions comprising such FX variants might therefore entail a thrombogenic risk.

One problem addressed in the present invention is to identify haemostatic bypassing agents. In particular, there is a need for haemostatic bypassing agents, which can be used to treat patients having a high titer of factor VIII inhibitors.

DETAILED DESCRIPTION

In the present invention it has been surprisingly found that biologically active factor X variants having enhanced haemostatic bypassing activity can be obtained by inserting an additional protease cleavage site C-terminal to Ile235 into the heavy chain of factor X. This additional protease cleavage site can be derived from human as well as from other mammalian proteins.

One aspect of the invention are modified biologically active recombinant factor X variants wherein one modification consists of an insertion of an additional cleavage site for a protease, and wherein the additional cleavage site is inserted C-terminal to Ile235 into the heavy chain of factor X. Cleavage by said protease of the additional cleavage site leads to activation of the factor X variant in addition to potential activation through cleavage of the natural cleavage site. The factor X variants of the present invention may have additional modifications, in particular in other regions of the factor X sequence. Accordingly, the insertion into the heavy chain of factor X may be one of several modifications to the amino acid sequence as compared to the wild type sequence as shown in SEQ ID NO:2.

In another aspect of the present invention, the natural factor X activation peptide in the modified biologically active recombinant factor X variants is modified such that proteases, which naturally activate factor X, are no longer able to cleave and activate said factor X variant. This may be achieved by introducing mutations into the activation peptide sequence of factor X. Mutations include insertions, deletions and substitutions. Preferred are deletions and/or substitutions in the activation peptide sequence such that proteases, which naturally activate factor X, are no longer able to cleave and activate said factor X variant, such that activation occurs only via the additional cleavage site.

According to preferred embodiments of the present invention the new protease cleavage site in the heavy chain of said modified factor X variant can be cleaved by a serine protease. More preferably, the serine protease is selected from the group consisting of factor IIa, factor IXa, factor Xa, factor XIa, factor XIIa, activated protein C, elastase or kallikrein. The amino acid sequences which are recognized and cleaved by these serine proteases are known to one of ordinary skill (e.g. as described in "Hemostasis and Thrombosis, Basic Principles and Clinical Practice", Fourth Edition, Colman et al. 2001 factor IIa: p 34-35, p 176, factor IXa: p 40-41, factor Xa: p 34-35, factor XIa p 128-129, factor XIIa: p 194, aPC: p 34-35, p 159, kallikrein: p 103-104 or elastase (O'Reilly et al., 1999; Antiangiogenic activity of the cleaved conformation of the serpin antithrombin: Science, 285, 1926-1928).

The insertion into the heavy chain of factor X may comprise one or more additional amino acids, which are not necessary for cleavage. These additional amino acids may be at the N-terminal and/or at the C-terminal end of the insertion. Accordingly, the insertion into the heavy chain may be represented by the following formula:

$$-R^1-P-R^2-,$$

wherein P designates the amino acid sequence recognized and cleaved by the cleaving protease (i.e. the cleavage site), $R^1$ designates a chemical bond or one or more amino acids (e.g. 1 to 10 amino acids), and
$R^2$ designates a chemical bond or one or more amino acids (e.g. 1 to 5 amino acids).

P has a length of at least 3 amino acids and preferably not more than 20 amino acids. Preferably, $R^1$ is a chemical bond or consists of 1, 2 or 3 amino acids. It is further preferred that $R^2$ is a chemical bond or consists of 1 or 2 amino acids. It is most preferred that the amino acid C-terminal to the chemical bond which is cleaved when the newly introduced protease cleavage site is cleaved is isoleucine. Also preferred is valine instead of said isoleucine. Other preferred amino acids C-terminal instead of said isoleucine are alanine, serine or threonine.

Suitable amino acid sequences which may be inserted into the heavy chain include but are not limited to those which can be recognized and cleaved by serine proteases as listed in table 1 below:

TABLE 1

Examples for cleavage site insertions

| cleavage site derived from | sequence | SEQ ID NO |
|---|---|---|
| human FVII | NASKPQGRI | SEQ ID NO 17 |
|  | KRNASKPQGRI | SEQ ID NO 18 |
|  | LEKRNASKPQGRI | SEQ ID NO 19 |
|  | NQASKPQGRV | SEQ ID NO 20 |
|  | KRNASKPQGRV | SEQ ID NO 21 |
| human FIX | TQSTQSFNDFTRV | SEQ ID NO 22 |
|  | TQSFNDFTRV | SEQ ID NO 23 |
|  | SFNDFTRV | SEQ ID NO 24 |
|  | NDFTRV | SEQ ID NO 25 |
|  | FTRV | SEQ ID NO 26 |

TABLE 1-continued

Examples for cleavage site insertions

| cleavage site derived from | sequence | SEQ ID NO |
|---|---|---|
|  | TQSTQSFNDFTRI | SEQ ID NO 27 |
|  | TQSFNDFTRI | SEQ ID NO 28 |
|  | SFNDFTRI | SEQ ID NO 29 |
|  | NDFTRI | SEQ ID NO 30 |
|  | FTRI | SEQ ID NO 31 |
| bovine FIX | NQSFDEFSRI | SEQ ID NO 32 |
| canine FIX | TQPLNDFTRI | SEQ ID NO 33 |
| murine FIX | SESLNDFTRI | SEQ ID NO 34 |
| rabbit FIX | SQSSDDFTRI | SEQ ID NO 35 |
| human ATIII reactive site loop | GSEAAASTAV VIAGRI | SEQ ID NO 36 |
|  | GSEAAASTAV VIAGRSI | SEQ ID NO 37 |
|  | GSEAAASTAV VIAGRV | SEQ ID NO 38 |

The inserted amino acid sequence ($-R^1-P-R^2-$), encompasses at least 3 amino acids. Preferably, the amino acid insertion comprising the cleavage site consists of 3 to 50, more preferably of 4 to 30, more preferably of 4 to 20, most preferably of 5 to 15. Moreover fragments of protease cleavage sites are also encompassed by the invention, as exemplified in a series of deletion mutants of the protease cleavage site from factor IX (SEQ ID NO 22 to SEQ ID NO 31 in table 1), as long as the FX variant comprising such fragmented protease cleavage site is still susceptible to cleavage and said FX variant still has biological activity.

In one preferred embodiment, the additional cleavage site is inserted between Ile235 and Val236 of the factor X sequence. Alternatively, the additional cleavage site may be inserted between two amino acids, which are closer to the C-terminus of the factor X sequence. For example, the additional cleavage site may be inserted between Val236 and Gly237, or between Gly237 and Gly238 of the factor X sequence.

The factor X variants of the invention have biological activity. The term "biological activity" as used herein refers to factor X activity. A protein having factor X activity means, that the protein in its zymogen form can be activated through cleavage by a protease and has in its activated form factor Xa activity. Factor X activity can be determined in a coagulation assay in vitro. For example, factor X activity can be determined in a prothrombin time (PT) assay measuring the activity of the extrinsic coagulation pathway, as described in Example 4. Factor X activity expressed as clotting activity in a sample is given as mU/ml.

The factor X activity so determined may be referred to the amount of factor X antigen present in the sample, thus yielding the "specific activity" of the variant, expressed exemplary in U/mg or mU/µg protein. The specific activity of the variants of the invention is preferably at least 50%, more preferably at least 75% of the factor X activity of a recombinant factor X molecule having the wild type sequence as shown in SEQ ID NO:2.

The factor X variants of the invention further have haemostatic bypassing activity. This activity can be determined as described in Example 4 by measuring the clotting activity (aPPT) using FVIII- or FIX-depleted plasma. The clotting activity in such assays is preferably more than 70 fold, more preferably 100 fold increased, most preferably more than 500 fold of that of recombinant factor X having the wild type sequence.

Preferred modified biologically active recombinant factor X variants according to the invention are factor X variants which have enhanced haemostatic bypassing activity compared to factor X variants with a modification within the sequence of the naturally occurring factor X activation cleavage peptide, said modification representing a cleavage site of a protease which does not naturally cleave in this area of the factor X sequence and which upon cleavage of said additional cleavage site activates said factor X variant.

Another aspect of the invention is a method for producing a haemostatic bypassing agent, comprising inserting a protease cleavage site into the heavy chain of the factor X amino acid sequence. Preferably, the cleavage site is inserted C-terminal to Ile235. The preferred embodiments of this method correspond to the preferred embodiments of the factor X variant described herein.

The invention further relates to a polynucleotide encoding a modified human factor X as described in this application. The term "polynucleotide(s)" generally refers to any polyribonucleotide or polydeoxyribonucleotide that may be unmodified RNA or DNA or modified RNA or DNA. The polynucleotide may be single- or double-stranded DNA, single or double-stranded RNA. As used herein, the term "polynucleotide(s)" also includes DNAs or RNAs that comprise one or more modified bases and/or unusual bases, such as inosine. It will be appreciated that a variety of modifications may be made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells.

The skilled person will understand that, due to the degeneracy of the genetic code, a given polypeptide can be encoded by different polynucleotides. These "variants" are encompassed by this invention.

Preferably, the polynucleotide of the invention is an isolated polynucleotide. The term "isolated" polynucleotide refers to a polynucleotide that is substantially free from other nucleic acid sequences, such as and not limited to other chromosomal and extra-chromosomal DNA and RNA. Isolated polynucleotides may be purified from a host cell. Conventional nucleic acid purification methods known to skilled artisans may be used to obtain isolated polynucleotides. The term also includes recombinant polynucleotides and chemically synthesized polynucleotides.

Yet another aspect of the invention is a plasmid or vector comprising a polynucleotide according to the invention. Preferably, the plasmid or vector is an expression vector. In a particular embodiment, the vector is a transfer vector for use in human gene therapy.

Still another aspect of the invention is a host cell comprising a polynucleotide of the invention or a plasmid or vector of the invention.

The host cells of the invention may be employed in a method of producing a modified homologue of human factor X, which is part of this invention. The method comprises:

a) culturing host cells of the invention under conditions such that the modified homologue of human factor X is expressed; and b) optionally recovering the modified homologue of human factor X from the host cells or from the culture medium.

Degree and location of glycosylation or other post-translation modifications may vary depending on the chosen host cells and the nature of the host cellular environment. When referring to specific amino acid sequences, posttranslational modifications of such sequences are encompassed in this application.

"Factor X" as used in this application means a product consisting of the nonactivated form (factor X). "Factor X" within the above definition includes proteins that have the amino acid sequence of native human factor X. It also includes proteins with a slightly modified amino acid sequence, for instance, a modified N-terminal end including N-terminal amino acid deletions or additions so long as those proteins substantially retain the activity of factor Xa. "Factor X" within the above definition also includes natural allelic variations that may exist and occur from one individual to another. "Factor X" within the above definition further includes variants of factor X. Such variants differ in one or more amino acid residues from the wild type sequence. Examples of such differences may include truncation of the N- and/or C-terminus by one or more amino acid residues (e.g. 1 to 10 amino acid residues), or addition of one or more extra residues at the N- and/or C-terminus, e.g. addition of a methionine residue at the N-terminus, as well as conservative amino acid substitutions, i.e. substitutions performed within groups of amino acids with similar characteristics, e.g. (1) small amino acids, (2) acidic amino acids, (3) polar amino acids, (4) basic amino acids, (5) hydrophobic amino acids, (6) aromatic amino acids. Examples of such conservative substitutions are shown in table 2.

TABLE 2

Examples of conservative substitutions

| | | | | |
|---|---|---|---|---|
| (1) | Alanine | Glycine | | |
| (2) | Aspartic acid | Glutamic acid | | |
| (3a) | Asparagine | Glutamine | | |
| (4) | Arginine | Histidine | Lysine | |
| (5) | Isoleucine | Leucine | Methionine | Valine |
| (6) | Phenylalanine | Tyrosine | Tryptophane | |

The term "recombinant" means, for example, that the variant has been produced in a host organism by genetic engineering techniques.

Expression of the Proposed Variants:

The production of recombinant proteins at high levels in suitable host cells, requires the assembly of the above-mentioned modified cDNAs into efficient transcriptional units together with suitable regulatory elements in a recombinant expression vector, that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-poiyadenylation sequence. Preferably, this sequence is derived from the Simian Virus 40 early transcriptional region, the rabbit beta-globin gene, or the human tissue plasminogen activator gene.

The cDNAs are then integrated into the genome of a suitable host cell line for expression of the factor X variant. Preferably this cell line should be an animal cell-line of vertebrate origin in order to ensure correct folding, Gla-domain synthesis, disulfide bond formation, asparagine-linked glycosylation, O-linked glycosylation, and other post-translational modifications as well as secretion into the cultivation medium. Examples of other post-translational modifications are hydroxylation and proteolytic processing of the nascent polypeptide chain. Examples of cell lines that can be used are monkey COS-cells, mouse L-cells, mouse C127-cells, hamster BHK-21 cells, human embryonic kidney 293 cells, and preferentially hamster CHO— cells.

The recombinant expression vector encoding the corresponding cDNAs can be introduced into an animal cell line in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNAs can also be introduced into animal cells together with another recombinant gene which may function as a dominant selectable marker in these cells in order to facilitate the isolation of specific cell clones which have integrated the recombinant DNA into their genome. Examples of this type of dominant selectable marker genes are Tn5 amino glycoside phosphotransferase, conferring resistance to geneticin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated into the genome of the host cell, frequently resulting in a tight physical linkage between the different transcription units.

Other types of selectable marker genes, which can be used together with the cDNA of the desired protein, are based on various transcription units encoding dihydrofolate reductase (dhfr). After introduction of this type of gene into cells lacking endogenous dhfr-activity, preferentially CHO-cells (DUKX-B11, DG-44) it will enable these to grow in media lacking nucleosides. An example of such a medium is Ham's F12 without hypoxanthine, thymidin, and glycine. These dhfr-genes can be introduced together with the coagulation factor cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a bath culture or as a perfusion culture with continuous production of conditioned medium over extended periods of time. Thus, according to the present invention, the above cell lines are well suited for the development of an industrial process for the production of the desired recombinant proteins The recombinant protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant protein to a monoclonal antibody, which is immobilised on a solid support. After desorption, the protein can be further purified by a variety of chromatographic techniques based on the above properties.

It is preferred to purify the modified biologically active factor X variant of the present invention to ≥80% purity, more preferably ≥95% purity, and particularly preferred is a pharmaceutically pure state that is greater than 99.9% pure with respect to contaminating macromolecules, particularly other proteins and nucleic acids, and free of infectious and pyrogenic agents. Preferably, an isolated or purified modified biologically active factor X variant of the invention is substantially free of other polypeptides.

The recombinant proteins described in this invention can be formulated into pharmaceutical preparations for therapeutic use. The purified proteins may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", $3^{rd}$ edition, Kibbe et al., Pharmaceutical Press (2000)). In particular, the pharmaceutical composition comprising the polypeptide variant of the invention may be formulated in lyophilized or stable soluble form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known an can be used to administer the composition by any convenient route. Preferentially the compositions of the invention are administered systemically. For systemic use, the factor X variants of the invention are formulated for parenteral (e.g. intravenous, subcutaneous, intramuscular, intraperitoneal, intracerebral, intrapulmonar, intranasal or transdermal) or enteral (e.g., oral, vaginal or rectal) delivery according to conventional methods. The most preferential route of administration is intravenous administration. The formulations can be administered continuously by infusion or by bolus injection. Some formulations encompass slow release systems.

The modified biologically active factor X variants of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g.

the indication, formulation, mode of administration and has to be determined in preclinical and clinical trials for each respective indication.

The pharmaceutical composition of the invention may be administered alone or in conjunction with other therapeutic agents. These agents may be incorporated as part of the same pharmaceutical.

Another aspect of the invention is the use of a modified homologue of human Factor X as described herein, of a polynucleotide of the invention, of a plasmid or vector of the invention, or of a host cell of the invention for the manufacture of a medicament for the treatment or prevention of a blood coagulation disorder. Blood coagulation disorders include but are not limited to hemophilia A, hemophilia B, or FVII/FVIIa deficiency. Preferably these diseases are caused or congenital forms are aggravated by autoimmune antibodies against the respective coagulation factors. In a specific embodiment, the patients to be treated have inhibitor antibodies against factor VIII. Preferably, the treatment comprises human gene therapy.

The invention also concerns a method of treating an individual suffering from a blood coagulation disorder such as hemophilia A, hemophilia B or FVII/FVIIa deficiency, preferably these diseases are caused by or congenital forms are aggravated by autoimmune antibodies against the respective coagulation factors. The method comprises administering to said individual an efficient amount of the modified homologue of human factor X as described herein. In another embodiment, the method comprises administering to the individual an efficient amount of the polynucleotide of the invention or of a plasmid or vector of the invention. Alternatively, the method may comprise administering to the individual an efficient amount of the host cells of the invention described herein.

DESCRIPTION OF THE TABLES AND DRAWINGS

FIG. 1: Outline of the nucleic acid sequence coding for the inserted protease cleavage site of the FX variant encoded by the construct pFX 619 as described in example 1 (pFX-532 contains nucleotides 658-714 of SEQ ID NO: 1 and residues 220-238 of SEQ ID NO: 2; pFX-619 contains SEQ ID NOS 39-40).

FIG. 2: Outline of FX wild type and of FX variants with newly introduced protease cleavage sites. Numbers refer to amino acid numbering of SEQ ID NO 2, the activation peptide being defined as the amino acid sequence between Arg182 and Ile235. pFX-532 contains residues 182-185 and 220-238 of SEQ ID NO: 2. pFX-535 contains SEQ ID NOS 41-42. pFX-641 contains SEQ ID NOS 43-44. pFX-619 contains SEQ ID NOS 45-46. pFX-635 contains SEQ ID NOS 47-48.

Foreign activation sequences derived from factor IX are outlined in bold letters. Underlined amino acids denote point mutations, which render the respective factor X molecule non-activatable by the tenase complex and factor VIIa/tissue factor, respectively. The construct "pFX-532" corresponds to the factor X wild type sequence.

FIG. 3: Nucleotide sequence and protein sequence of wild type factor X (SEQ ID NOs 1 and 2).

EXAMPLES

Example 1

Construction of Expression Plasmids

Factor X coding sequence was amplified by PCR from a human liver cDNA library (Ambion) using primers We1292 and We1293 (SEQ ID NO 3 and 4). In a second round of PCR using primers We1354 and We 1355 (SEQ ID NO 5 and 6) a cleavage site for restriction endonuclease NheI was introduced to the 5'-end and a cleavage site for restriction endonuclease NotI was introduced to the 3'-end of the fragment. The PCR fragment was then inserted into the NheI/NotI sites of pIRESpuro3 (BD Biosciences). The resulting plasmid was designated pFX-445.

To improve processing of the propeptide the cleavage site was improved by replacing amino acid threonine at position 39 (SEQ ID NO 2) by arginine (Rudolph et al., 1997 (Protein Expression and Purification 10:373-378)). For that, pFX-445 was subjected to site-directed mutagenesis using oligonucleotides We1482 and We 1483 (SEQ ID NO 7 and 8) according to standard methods (QuickChange XL Site Directed Mutagenesis Kit, Stratagene). The resulting plasmid was designated pFX-532.

All mutations described below were performed with a commercially available mutagenesis kit (QuickChange XL Site Directed Mutagenesis Kit, Stratagene). Based on pFX-532, constructs with factor XIa cleavage sites were generated. Replacement mutagenesis using oligonucleotides We1444 and We 1445 (SEQ ID NO 9 and 10) resulted in plasmid pFX-535 with a replacement of 8 amino acids of the factor X activation region (amino acids 225-233 of SEQ ID NO 2) by 8 amino acids from the activation region of FIX (FIG. 3).

Insertion mutagenesis using oligonucleotides We1561a and We 1562a (SEQ ID NO 11 and 12) resulted in plasmid pFX-619 with an insertion of 10 amino acids of the FIX activation region between factor X amino acid position 235 and 236 (SEQ ID NO 2).

Site directed mutagenesis using oligonucleotides We1567 and We1568 (SEQ ID NO 13 and 14) on pFX-532 was used to generate plasmid pFX-641. It contained two mutations within the factor X activation peptide, Leu232Asp and Thr233Asp, thereby generating a factor X molecule, which could not be activated. Similarly, primers We1587 and We1588 (SEQ ID NO 15 and 16) were applied on plasmid pFX-619, thus generating plasmid pFX-635 (FIG. 2)

Example 2

Transfection and Expression of Modified Factor X Molecules

Plasmids were grown up in *E. coli* TOP10 (Invitrogen) and purified using standard protocols (Qiagen). HEK 293 cells were transfected using the Lipofectamine 2000 reagent (Invitrogen) and grown up in serum-free medium (Invitrogen 293 Express) in the presence of 50 ng/ml Vitamin K and 4 µg/ml Puromycin. About four weeks post transfection supernatants were harvested for biochemical characterization.

Example 3

Characterization of Recombinant Factor X Variants

The expression of the factor X variants was controlled by quantitative ELISA using monoclonal antibodies against factor X. Integrity of the recombinant proteins was analysed subsequently by SDS-PAGE and Western blotting. Samples were analysed under reduced and non-reduced conditions. Plasmatic factor X served as a native molecular weight control, factor Xa was used to detect and compare any activated recombinant factor X variants in case of auto-activation. As visualized in Western blots, all recombinant factor X variants were expressed with the correct molecular weight of about 58 kDa, and migrated at a comparable position to plasmatic factor X. When reduced, the recombinant factor X variants disintegrated into a heavy chain (HC) of approximately 40 kDa and a light chain (LC) of approximately 20 kDa. The 58 kDa band represented unprocessed one-chain (OC) factor X. There was neither factor Xa nor any aggregates of factor X detected in the Western blots.

Example 4

Investigation of In Vitro Activities of the Recombinant Factor X Variants in Human Factor X-, Factor VIII- and Factor IX Deficient Plasmas, as Well as in Human Inhibitor Plasma Factor X activity was determined in prothrombin time (PT) assay measuring the activity of the extrinsic coagulation pathway. 100 µl of factor X deficient plasma was mixed with 100 µl of factor X variant cell culture supernatant or purified protein. After incubation for 60 seconds at 37° C. 200 µl of Thromborel (Dade Behring), containing human plasma derived thromboplastin, $CaCl_2$ and phospholipids, was added to the mixture and clotting time in seconds determined by using a Schnittger & Gross coagulation timer. For determination of factor X activity, the assay was calibrated using a plasmatic factor X standard. Cell culture supernatants of mutated factor X pFX-641 can serve as negative control for this assay. This mutant harbours a disabled cleavage site within the wild type factor X activation peptide like the one in pFX635. As expected when the mutant was tested at antigen levels equivalent to 216.4 U/ml factor X, the clotting activity reached only 0.5 mU/ml.

Recombinant wild type factor X derived from pFX532 as well as factor X variants derived from pFX535, pFX619, and pFX635 were purified and antigen determined by ELISA using antibodies specific for factor X antigen concentrations ranged from 2.8 up to 4.3 U/ml To exclude the disturbance of the measurement of factor X by factor Xa, factor Xa was determined by a chromogenic assay (DADE Behring). All purified factor X variants contained only factor Xa levels of 0.028-0.051 mU/ml (Table 3), not significantly interfering with the factor X determination.

In order to compare the expressed factor X variants among each other, factor X clotting activities were determined and adjusted to about 1.5 mU/ml. All the variants tested were functional active, resulting in clotting activities between 1.48 and 1.72 mU/ml (Table 3).

Functionality of recombinant factor X variants in FVIII- and FIX deficient plasmas was tested in activated partial prothrombin time (aPPT) measuring the activity of the intrinsic coagulation cascade. 100 µl of FVIII- or FIX-depleted plasma was mixed with 100 µl of factor X variant cell culture supernatant or purified protein. After incubation for 6 minutes at 37° C. 100 µl of Pathromptin (Dade Behring) containing $SiO_2$, phospholipids and 40 mM $NaCl_1$ as well as 100 µl of 25 mM $CaCl_2$ was added to start the coagulation reaction. Clotting time in seconds was determined by using a Schnittger & Gross coagulation timer. Activity was expressed as respective clotting FX equivalents as compared to standard human plasma. The recombinant wild type factor X reached clotting activities of only 6.6 mU/ml in factor VIII depleted plasma and of only 5.8 mU/ml in FIX depleted plasma, as expected. In contrast, the factor X variants reached clotting activities ranging from 423.7 to 8545.8 mU/ml in factor VIII depleted plasma and from 272.3 mIU/ml to 4620.2 mIU/ml in FIX depleted plasma. This demonstrates the functionality of the inserted Factor XIa cleavage site, changing FX into a clotting active haemostatic bypassing agent (Table 3).

Surprisingly, and albeit all recombinant factor X variants were adjusted to factor X clotting activities factor X variants derived from pFX-619 and pFX635 developed strong clotting activities of 8545.8 and 2692.0 mil/ml respectively, while the factor X variant derived from pFX535 reached only 423.7 in FVIII depleted plasma (Table 2). Variants derived from pFX619 and pFX635 differ from pFX535 in that in pFX-619 and pFX-635 the new factor IX activation sequence has been inserted at the amino terminus of the heavy chain C-terminal of IIe235 while maintaining the complete activation peptide sequence of factor X. Factor X variant derived from pFX535 corresponds to factor X variants described in WO 01/10896 having the new factor IX activation sequence inserted within the region of the wild-type FX activation peptide N-terminal to IIe235, whereas pFX619 and pFX635 are factor X variants of the present invention. Interestingly, factor X variants encoded by pFX619 and pFX635 developed also strong clotting activities of 4620.2 and 1644.8 mU/ml respectively in FIX depleted plasma, while the factor X variant derived from pFX535 reached only 272.3 mU/ml confirming the results obtained in the FVIII or FIX clotting assay based on plasma depleted from FVIII or FIX respectively. (Table 2).

Determination of functional activity was further performed using FVIII-inhibitor containing plasma from a haemophilia A patient. The patient plasma contained about 300 Bethesda Units of FVIII inhibitors per ml. Clotting was determined in aPPT and samples adjusted to factor X clotting as described above.

While the sample buffer control used for dilution of standards and test samples reached coagulation times of 156.5 seconds, recombinant wild type factor X reached coagulation times of 111.4 seconds. Confirming the surprising results in the FVIII or FIX clotting assay based on plasma depleted from FVIII or FIX factor X variants derived from pFX619 and pFX635 led in a FEIBA assay based on a plasma containing FVIII inhibitory antibodies to clotting times of 33.7 and 38.4 seconds being significantly shorter than the respective clotting times obtained when factor X variant pFX535 was used with 51.1 seconds.

Altogether, it was shown that the factor X variants were functionally active as haemostatic bypassing agents, and that these factor X variants show clotting activity in haemophilia A patient plasma containing inhibitors against factor VIII. To our surprise, factor X variants encoded by pFX619 and pFX635 showed much stronger clotting activity in factor VIII and factor IX depleted plasma, when compared to factor X variant encoded by pFX535 when adjusted to same factor X clotting equivalents.

TABLE 3

Determination of antigen and clotting activities of pFX532, pFX535, pFX619, and pFX635

| Proteins expressed | FX equivalence | | | Bypassing activities | | |
|---|---|---|---|---|---|---|
| | FX Antigen (ELISA) IU/ml | FX Activity (PT) IU/ml | FXa Activity (chromogenic assay) mIU/ml | Activity (aPPT) in FVIII depleted plasma mIU/ml | Activity (aPPT) in FIX depleted plasma mIU/ml | FEIBA Activity (in FVIII inhibitor containing plasma) Clotting time (sec.) |
| pFX532 (wild type) | 4.3 | 1.72 | 0.028 | 6.6 | 5.8 | 111.4 |
| pFX535 (comparison (WO 01/10896) | 3.5 | 1.62 | 0.023 | 423.7 | 272.3 | 51.1 |
| pFX619 (example) | 2.8 | 1.52 | 0.028 | 8545.8 | 4620.2 | 33.7 |
| pFX635 (example) | 3.4 | 1.48 | 0.051 | 2692.0 | 1644.8 | 38.4 |

Example 5

Purification of Recombinant Factor X Variants by Monoclonal Antibody Affinity Chromatography Purification of recombinant factor X variant pFX635 serves as an example for all the factor X variants purified. Monoclonal antibodies FX-13 (ZLB Behring), specific for factor X, were coupled to CNBr-activated Sepharose. The resulting affinity resin was pored into a Pharmacia XK 16 chromatography column to form an affinity matrix of 1.6 cm in diameter and 1.8 cm in height, resulting in 3.6 ml of gel. The affinity matrix was stored in 2.5M NaCl, 10 mM di-sodium-hydrogen-phosphate. Before use, the gel was equilibrated with 10 gel-volumes of 20 mM tri-sodium citrate, 0.15M NaCl at pH 7.0-HCl.

Cell culture supernatant containing more than 100 mIU/ml factor X-antigen was dialysed using a VISKING tubing type 32/36, in 2-4 l of equilibration buffer at 4-8° C. over night.

Affinity-gel was loaded with 70 ml dialyzed supernatant at flow rates of 1 ml/min. Gel was washed with 10 volumes of equilibration buffer and subsequently eluted by 0.1 M glycine, pH 2.5-HCl. The eluted material was neutralized by NaOH and stabilized by 1.0M NaCl and 0.1 mg/ml sodium caprylate.

Samples from cell culture supernatant of factor X variant pFX635, from the flow threw fraction and from the eluted material were analysed by SDS-PAGE and subsequent silver staining. A 58 kDa protein band was purified by the method described above. The 58 kDa band resembles factor X variant 635, as confirmed by Western blotting probed by anti-factor X antibodies.

What is claimed is:

1. A modified biologically active recombinant factor X variant comprising a factor X polypeptide, wherein the factor X polypeptide comprises the factor X heavy chain sequence of SEQ ID NO: 2, with the addition of one or more cleavage sites for a protease inserted into the factor X heavy chain sequence between at least one set of amino acids selected from the group consisting of amino acids Ile235 and Val236, amino acids Val236 and Gly237 and amino acids Gly237 and Gly238, wherein the modified factor X variant is activated upon cleavage of the one or more inserted cleavage sites by the protease, and wherein the modified factor X variant has factor X clotting activity.

2. The modified biologically active recombinant factor X variant of claim 1, wherein a protease that cleaves the one or more cleavage sites does not activate wild-type factor X.

3. The modified biologically active recombinant factor X variant of claim 1, further comprising a factor X activation peptide that has been modified, wherein the modification renders the modified factor X variant comprising the modified factor X activation peptide resistant to cleavage and activation by proteases that cleave and activate wild-type factor X, wherein the modified factor X activation peptide comprises Ser183 to Arg234 of SEQ ID NQ: 2 with a mutation of at least one of amino acids Leu232 and Thr233.

4. The modified biologically active recombinant factor X variant of claim 1, wherein the one or more inserted cleavage sites are for a serine protease.

5. The modified biologically active recombinant factor X variant of claim 4, wherein the one or more inserted cleavage sites are for factor IIa, factor IXa, factor Xa, factor XIa, factor XIIa, activated protein C, elastase, or kallikrein.

6. The modified biologically active recombinant factor X variant of claim 1, wherein the one or more inserted protease cleavage sites each encompass at least 3 amino acids.

7. A pharmaceutical composition comprising the modified biologically active recombinant factor X variant of claim 1.

8. The modified biologically active recombinant factor X variant of claim 1, wherein the one or more inserted cleavage sites are the only modification as compared to the wild-type factor X sequence.

9. The modified biologically active recombinant factor X variant of claim 1, wherein the inserted protease cleavage site is between the factor X heavy chain amino acids Ile235 and Val236, wherein the factor X heavy chain amino acids Leu232 and Thr233 are each replaced with Asp, and wherein the inserted protease cleavage site and the Leu232Asp and Thr233Asp mutations are the only modifications as compared to the wild-type factor X sequence.

* * * * *

```
                        SEQUENCE LISTING

<160> NUMBER OF SEQ ID NOS: 48

<210> SEQ ID NO 1
<211> LENGTH: 1467
<212> TYPE: DNA
<213> ORGANISM: Homo sapiens
<220> FEATURE:
<221> NAME/KEY: CDS
<222> LOCATION: (1)..(1464)

<400> SEQUENCE: 1 atg ggg cgc cca ctg cac ctc gtc ctg ctc agt gcc tcc ctg gct ggc      48
Met Gly Arg Pro Leu His Leu Val Leu Leu Ser Ala Ser Leu Ala Gly
1               5                   10                  15 ctc ctg ctc ctc ggg gaa agt ctg ttc atc cgc agg gag cag gcc aac      96
Leu Leu Leu Leu Gly Glu Ser Leu Phe Ile Arg Arg Glu Gln Ala Asn
            20                  25                  30 aac atc ctg gcg agg gtc acg agg gcc aat tcc ttt ctt gaa gag atg     144
Asn Ile Leu Ala Arg Val Thr Arg Ala Asn Ser Phe Leu Glu Glu Met
        35                  40                  45 aag aaa gga cac ctc gaa aga gag tgc atg gaa gag acc tgc tca tac     192
Lys Lys Gly His Leu Glu Arg Glu Cys Met Glu Glu Thr Cys Ser Tyr
    50                  55                  60 gaa gag gcc cgc gag gtc ttt gag gac agc gac aag acg aat gaa ttc     240
Glu Glu Ala Arg Glu Val Phe Glu Asp Ser Asp Lys Thr Asn Glu Phe
65                  70                  75                  80 tgg aat aaa tac aaa gat ggc gac cag tgt gag acc agt cct tgc cag     288
Trp Asn Lys Tyr Lys Asp Gly Asp Gln Cys Glu Thr Ser Pro Cys Gln
                85                  90                  95
```

-continued

| | | |
|---|---|---|
| aac cag ggc aaa tgt aaa gac ggc ctc ggg gaa tac acc tgc acc tgt<br>Asn Gln Gly Lys Cys Lys Asp Gly Leu Gly Glu Tyr Thr Cys Thr Cys<br>100                             105                      110 | 336 |
| tta gaa gga ttc gaa ggc aaa aac tgt gaa tta ttc aca cgg aag ctc<br>Leu Glu Gly Phe Glu Gly Lys Asn Cys Glu Leu Phe Thr Arg Lys Leu<br>         115                         120                  125 | 384 |
| tgc agc ctg gac aac ggg gac tgt gac cag ttc tgc cac gag gaa cag<br>Cys Ser Leu Asp Asn Gly Asp Cys Asp Gln Phe Cys His Glu Glu Gln<br>130                             135                     140 | 432 |
| aac tct gtg gtg tgc tcc tgc gcc cgc ggg tac acc ctg gct gac aac<br>Asn Ser Val Val Cys Ser Cys Ala Arg Gly Tyr Thr Leu Ala Asp Asn<br>145                             150                  155                    160 | 480 |
| ggc aag gcc tgc att ccc aca ggg ccc tac ccc tgt ggg aaa cag acc<br>Gly Lys Ala Cys Ile Pro Thr Gly Pro Tyr Pro Cys Gly Lys Gln Thr<br>                   165                      170                  175 | 528 |
| ctg gaa cgc agg aag agg tca gtg gcc cag gcc acc agc agc agc ggg<br>Leu Glu Arg Arg Lys Arg Ser Val Ala Gln Ala Thr Ser Ser Ser Gly<br>         180                         185                  190 | 576 |
| gag gcc cct gac agc atc aca tgg aag cca tat gat gca gcc gac ctg<br>Glu Ala Pro Asp Ser Ile Thr Trp Lys Pro Tyr Asp Ala Ala Asp Leu<br>                195                      200                  205 | 624 |
| gac ccc acc gag aac ccc ttc gac ctg ctt gac ttc aac cag acg cag<br>Asp Pro Thr Glu Asn Pro Phe Asp Leu Leu Asp Phe Asn Gln Thr Gln<br>210                             215                     220 | 672 |
| cct gag agg ggc gac aac aac ctc acc agg atc gtg gga ggc cag gaa<br>Pro Glu Arg Gly Asp Asn Asn Leu Thr Arg Ile Val Gly Gly Gln Glu<br>225                             230                  235                    240 | 720 |
| tgc aag gac ggg gag tgt ccc tgg cag gcc ctg ctc atc aat gag gaa<br>Cys Lys Asp Gly Glu Cys Pro Trp Gln Ala Leu Leu Ile Asn Glu Glu<br>                     245                      250                  255 | 768 |
| aac gag ggt ttc tgt ggt gga acc att ctg agc gag ttc tac atc cta<br>Asn Glu Gly Phe Cys Gly Gly Thr Ile Leu Ser Glu Phe Tyr Ile Leu<br>                     260                      265                  270 | 816 |
| acg gca gcc cac tgt ctc tac caa gcc aag aga ttc aag gtg agg gta<br>Thr Ala Ala His Cys Leu Tyr Gln Ala Lys Arg Phe Lys Val Arg Val<br>275                             280                  285 | 864 |
| ggg gac cgg aac acg gag cag gag gag ggc ggt gag gcg gtg cac gag<br>Gly Asp Arg Asn Thr Glu Gln Glu Glu Gly Gly Glu Ala Val His Glu<br>         290                         295                  300 | 912 |
| gtg gag gtg gtc atc aag cac aac cgg ttc aca aag gag acc tat gac<br>Val Glu Val Val Ile Lys His Asn Arg Phe Thr Lys Glu Thr Tyr Asp<br>305                             310                     315                    320 | 960 |
| ttc gac atc gcc gtg ctc cgg ctc aag acc ccc atc acc ttc cgc atg<br>Phe Asp Ile Ala Val Leu Arg Leu Lys Thr Pro Ile Thr Phe Arg Met<br>                   325                      330                  335 | 1008 |
| aac gtg gcg cct gcc tgc ctc ccc gag cgt gac tgg gcc gag tcc acg<br>Asn Val Ala Pro Ala Cys Leu Pro Glu Arg Asp Trp Ala Glu Ser Thr<br>                   340                      345                  350 | 1056 |
| ctg atg acg cag aag acg ggg att gtg agc ggc ttc ggg cgc acc cac<br>Leu Met Thr Gln Lys Thr Gly Ile Val Ser Gly Phe Gly Arg Thr His<br>355                             360                     365 | 1104 |
| gag aag ggc cgg cag tcc acc agg ctc aag atg ctg gag gtg ccc tac<br>Glu Lys Gly Arg Gln Ser Thr Arg Leu Lys Met Leu Glu Val Pro Tyr<br>         370                         375                  380 | 1152 |
| gtg gac cgc aac agc tgc aag ctg tcc agc agc ttc atc atc acc cag<br>Val Asp Arg Asn Ser Cys Lys Leu Ser Ser Ser Phe Ile Ile Thr Gln<br>385                             390                     395                    400 | 1200 |
| aac atg ttc tgt gcc ggc tac gac acc aag cag gag gat gcc tgc cag<br>Asn Met Phe Cys Ala Gly Tyr Asp Thr Lys Gln Glu Asp Ala Cys Gln<br>                   405                      410                  415 | 1248 |

```
ggg gac agc ggg ggc ccg cac gtc acc cgc ttc aag gac acc tac ttc      1296
Gly Asp Ser Gly Gly Pro His Val Thr Arg Phe Lys Asp Thr Tyr Phe
            420                 425                 430 gtg aca ggc atc gtc agc tgg gga gag ggc tgt gcc cgt aag ggg aag      1344
Val Thr Gly Ile Val Ser Trp Gly Glu Gly Cys Ala Arg Lys Gly Lys
        435                 440                 445 tac ggg atc tac acc aag gtc acc gcc ttc ctc aag tgg atc gac agg      1392
Tyr Gly Ile Tyr Thr Lys Val Thr Ala Phe Leu Lys Trp Ile Asp Arg
    450                 455                 460 tcc atg aaa acc agg ggc ttg ccc aag gcc aag agc cat gcc ccg gag      1440
Ser Met Lys Thr Arg Gly Leu Pro Lys Ala Lys Ser His Ala Pro Glu
465                 470                 475                 480 gtc ata acg tcc tct cca tta aag tga                                  1467
Val Ile Thr Ser Ser Pro Leu Lys
                485

<210> SEQ ID NO 2
<211> LENGTH: 488
<212> TYPE: PRT
<213> ORGANISM: Homo sapiens

<400> SEQUENCE: 2

Met Gly Arg Pro Leu His Leu Val Leu Leu Ser Ala Ser Leu Ala Gly
  1               5                  10                  15

Leu Leu Leu Leu Gly Glu Ser Leu Phe Ile Arg Arg Glu Gln Ala Asn
             20                  25                  30

Asn Ile Leu Ala Arg Val Thr Arg Ala Asn Ser Phe Leu Glu Glu Met
         35                  40                  45

Lys Lys Gly His Leu Glu Arg Glu Cys Met Glu Glu Thr Cys Ser Tyr
     50                  55                  60

Glu Glu Ala Arg Glu Val Phe Glu Asp Ser Asp Lys Thr Asn Glu Phe
 65                  70                  75                  80

Trp Asn Lys Tyr Lys Asp Gly Asp Gln Cys Glu Thr Ser Pro Cys Gln
                 85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270
```

```
Thr Ala Ala His Cys Leu Tyr Gln Ala Lys Arg Phe Lys Val Arg Val
        275                 280                 285

Gly Asp Arg Asn Thr Glu Gln Glu Gly Gly Glu Ala Val His Glu
290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
                340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
                420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
        450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
cagggacaca gtactcggcc                                              20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
gagtgggatc tcactttaat gg                                           22

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
```

-continued gcggctagca tggggcgccc actgcacc                                          28

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gcggcggccg ctcactttaa tggagaggac gttatg                                 36

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
cctggcgagg gtcaggaggg ccaattc                                           27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gaattggccc tcctgaccct cgccagg                                           27

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
cagacgcagc ctacccaatc atttaatgac ttcactcgga tcgtgggagg                  50

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
cctcccacga tccgagtgaa gtcattaaat gattgggtag gctgcgtctg                  50

<210> SEQ ID NO 11
<211> LENGTH: 55
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11

```
caacctcacc aggatcaccc agagcttcaa cgacttcacc cgcattgtgg gaggc         55
```

```
<210> SEQ ID NO 12
<211> LENGTH: 55
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
gcctcccaca atgcgggtga agtcgttgaa gctctgggtg atcctggtga ggttg         55
```

```
<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
ggcgacaaca acgacgacag gatcgtgg                                       28
```

```
<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
ccacgatcct gtcgtcgttg ttgtcgcc                                       28
```

```
<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
ggcgacaaca acgatgacag gatcacccag                                     30
```

```
<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
ctgggtgatc ctgtcatcgt tgttgtcgcc                                     30
```

```
<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Asn Ala Ser Lys Pro Gln Gly Arg Ile
```

```
<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Lys Arg Asn Ala Ser Lys Pro Gln Gly Arg Ile
 1               5                  10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Leu Glu Lys Arg Asn Ala Ser Lys Pro Gln Gly Arg Ile
 1               5                  10

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

Asn Ala Ser Lys Pro Gln Gly Arg Val
 1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

Lys Arg Asn Ala Ser Lys Pro Gln Gly Arg Val
 1               5                  10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

Thr Gln Ser Thr Gln Ser Phe Asn Asp Phe Thr Arg Val
 1               5                  10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
                          Peptide

<400> SEQUENCE: 23

Thr Gln Ser Phe Asn Asp Phe Thr Arg Val
  1               5                  10

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

Ser Phe Asn Asp Phe Thr Arg Val
  1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

Asn Asp Phe Thr Arg Val
  1               5

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 26

Phe Thr Arg Val
  1

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 27

Thr Gln Ser Thr Gln Ser Phe Asn Asp Phe Thr Arg Ile
  1               5                  10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 28

Thr Gln Ser Phe Asn Asp Phe Thr Arg Ile
  1               5                  10

<210> SEQ ID NO 29
```

<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 29

Ser Phe Asn Asp Phe Thr Arg Ile
  1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 30

Asn Asp Phe Thr Arg Ile
  1               5

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 31

Phe Thr Arg Ile
  1

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 32

Asn Gln Ser Phe Asp Glu Phe Ser Arg Ile
  1               5                  10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 33

Thr Gln Pro Leu Asn Asp Phe Thr Arg Ile
  1               5                  10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 34

Ser Glu Ser Leu Asn Asp Phe Thr Arg Ile
 1               5                  10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

Ser Gln Ser Ser Asp Asp Phe Thr Arg Ile
 1               5                  10

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 36

Gly Ser Glu Ala Ala Ala Ser Thr Ala Val Val Ile Ala Gly Arg Ile
 1               5                  10                  15

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 37

Gly Ser Glu Ala Ala Ala Ser Thr Ala Val Val Ile Ala Gly Arg Ser
 1               5                  10                  15
Ile

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 38

Gly Ser Glu Ala Ala Ala Ser Thr Ala Val Val Ile Ala Gly Arg Val
 1               5                  10                  15

<210> SEQ ID NO 39
<211> LENGTH: 87
<212> TYPE: DNA
<213> ORGANISM: Artificial Sequence
<220> FEATURE:
<223> OTHER INFORMATION: Description of Artificial Sequence: Synthetic
      Construct
<220> FEATURE:
<221> NAME/KEY: CDS
<222> LOCATION: (1)..(87)

<400> SEQUENCE: 39 ttc aac cag acg cag cct gag agg ggc gac aac aac ctc acc agg atc      48
Phe Asn Gln Thr Gln Pro Glu Arg Gly Asp Asn Asn Leu Thr Arg Ile
 1               5                  10                  15

```
acc cag agc ttc aac gac ttc acc cgc att gtg gga ggc            87
Thr Gln Ser Phe Asn Asp Phe Thr Arg Ile Val Gly Gly
            20                  25
```

<210> SEQ ID NO 40
<211> LENGTH: 29
<212> TYPE: PRT
<213> ORGANISM: Artificial Sequence
<220> FEATURE:
<223> OTHER INFORMATION: Description of Artificial Sequence: Synthetic
      Construct

<400> SEQUENCE: 40

Phe Asn Gln Thr Gln Pro Glu Arg Gly Asp Asn Asn Leu Thr Arg Ile
 1               5                  10                  15

Thr Gln Ser Phe Asn Asp Phe Thr Arg Ile Val Gly Gly
            20                  25

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 41

Arg Ser Val Ala
 1

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 42

Phe Asn Gln Thr Gln Pro Thr Gln Ser Phe Asn Asp Phe Thr Arg Ile
 1               5                  10                  15

Val Gly Gly

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 43

Arg Ser Val Ala
 1

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 44

Phe Asn Gln Thr Gln Pro Glu Arg Gly Asp Asn Asn Asp Asp Arg Ile
 1               5                  10                  15

```
Val Gly Gly

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 45

Arg Ser Val Ala
  1

<210> SEQ ID NO 46
<211> LENGTH: 29
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 46

Phe Asn Gln Thr Gln Pro Glu Arg Gly Asp Asn Asn Leu Thr Arg Ile
  1               5                  10                  15

Thr Gln Ser Phe Asn Asp Phe Thr Arg Ile Val Gly Gly
             20                  25

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 47

Arg Ser Val Ala
  1

<210> SEQ ID NO 48
<211> LENGTH: 29
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 48

Phe Asn Gln Thr Gln Pro Glu Arg Gly Asp Asn Asn Asp Asp Arg Ile
  1               5                  10                  15

Thr Gln Ser Phe Asn Asp Phe Thr Arg Ile Val Gly Gly
             20                  25
```